United States Patent [19]

Kramer et al.

[11] 4,206,571
[45] Jun. 10, 1980

[54] BUNKER CLOSURE DOOR OPERATING MECHANISM

[75] Inventors: Rolf Kramer, Siegen; Felix Schneider; Gerhard Kampmann, both of Netphen, all of Fed. Rep. of Germany

[73] Assignee: Waggon Union GmbH, Fed. Rep. of Germany

[21] Appl. No.: 892,072

[22] Filed: Mar. 31, 1978

[30] Foreign Application Priority Data

Apr. 2, 1977 [DE] Fed. Rep. of Germany ....... 2714860

[51] Int. Cl.² .................. B60P 1/56; B61D 7/18; B61D 7/28
[52] U.S. Cl. ..................... 49/340; 49/248; 49/345; 105/284; 222/556; 298/30
[58] Field of Search .............. 105/283, 284, 290; 49/246, 248, 340, 345, 348; 222/505, 556; 298/24, 27, 29, 30

[56] References Cited

U.S. PATENT DOCUMENTS

| | | | |
|---|---|---|---|
| 672,076 | 4/1901 | Cowell | 105/284 X |
| 974,097 | 10/1910 | Seaberg | 105/290 X |
| 1,011,219 | 12/1911 | McKee | 105/284 X |
| 2,867,329 | 1/1959 | Miller | 49/340 |
| 3,440,761 | 4/1969 | Floehr | 105/290 |
| 3,717,110 | 2/1973 | Miller | 105/284 |
| 3,807,316 | 4/1974 | Miller | 105/284 X |

*Primary Examiner*—Howard Beltran
*Attorney, Agent, or Firm*—McGlew and Tuttle

[57] ABSTRACT

A bunker closure door mechanism for a bunker housing which has an opening with a seat around the opening which is closed by a closure door body, comprises, first and second spaced apart end levers which are pivotally connected between the housing and one end of the door. In addition, central levers are pivotally connected to the door body intermediate its length and pivotally connected at their opposite ends to a toggle lever which is pivotally mounted on the housing. The door body carries guide pins which are engageable in vertical slots of guide members supported on the bunker housing. By means of an actuator in the form of a fluid-pressure operated piston and cylinder connection, a guide rod is actuated to engage the central lever intermediate its length and to pivot it about its connection to the toggle lever and to also shift the toggle lever over its dead center position. The guide pins ensure that the door is held initially in engagement while the toggle lever is shifted beyond its dead end position to permit lowering of the central lever and the door and then subsequent shifting of the door on its pivotal connections by the end levers to a position at which it may be placed on the side of the bunker housing.

5 Claims, 4 Drawing Figures

BUNKER CLOSURE DOOR OPERATING MECHANISM

FIELD AND BACKGROUND OF THE INVENTION

This invention relates in general to the construction of bunkers and, in particular, to a new and useful bunker door closure mechanism.

DESCRIPTION OF THE PRIOR ART

In order to close vertically downwardly directed discharge openings of shipping containers, particularly if small discharge cross-sections are concerned, flat slide gates are preferably used. Because of the weight of the stored material acting on the gate in a closed position, such gates can be used only up to certain discharge cross-sections since, otherwise, the force needed to open the gates becomes excessive and problems arise with the mounting of the slider.

In order to close larger discharge openings of shipping containers, it is known to use a hinged cover which, in its closed position, applies horizontally from below against the discharge opening, and for opening, can be pivoted, by means of levers and links, downwardly and into a position adjacent the discharge opening. In a known design, such a cover or door is hinged by means of two levers which are fixed to the door centrally on the outside thereof, at opposite locations. These levers are acted upon through other levers by a pivotally mounted shaft extending horizontally laterally of the discharge opening and receiving its pivotal motion from a working cylinder, through still other levers. While pivoting the door for opening, the door is swung arcuately downwardly and then into a position adjacent the discharge opening.

This design is disadvantageous because the door is supported only in its central portion, so that with large discharge openings, it tends to twist and is thus susceptible to disturbances. Another disadvantage of this design is that, while opening, the door disengages from the closing edge of the discharge opening along its entire circumference. This causes the stored material to flow out, in the first door opening phase, past the door edge and to all sides, whereby, the material is dispersed over a larger area and, in addition, as the door is opened further, the door must traverse the stream of materials. The drawbacks of such a design are obvious.

The design of another bunker door is known which is substantially identical with that described in the foregoing, except that the door is not actuated through a shaft controlled by a working cylinder, but is instead actuated by means of a spindle acting on a crank lever. The opening motion and the support of the door, however, substantially correspond to the first-mentioned design. The disadvantages of the first mentioned design also apply to this mechanically actuated bunker door.

SUMMARY OF THE INVENTION

The present invention is directed to a bunker door for discharge openings provided at a lowermost location of shipping containers, which can be used for large discharge openings and ensures a reliability in service of the door by an exact guidance thereof with a minimum deflection of the stream of material during the opening operation and without traversing the opening while avoiding all of the other drawbacks of the prior art designs mentioned above.

In accordance with the invention, a bunker door is hinged through two links and two levers, so that the exact guidance of the door during the opening motion is ensured. The loads occurring on the door due to the stream of stored material are largely transmitted as normal forces through the links and levers. Bending forces are eliminated by the system of links. The guidance by the guide pins and guide members of the door in the first phase of the opening motion advantageously ensures that the door is first opened at one end and then is uniformly swung into a position adjacent the discharge opening. This prevents the stored material from flowing out past the door edges on all sides. There is no need for the door to traverse the stream of material during the opening motion. The fact that the pivotal motion of the lever is limited by a stop beyond the top dead center thereof provides a safe mechanical locking of the door in its closing position, because the pressure of the stored material acts on the levers in the closing direction. During the opening motion of the door, the fact that the pivotal motion of the lever is limited, limits the opening motion of the door about the links which, in this phase, act as hinges. During the further pivoting of the door, the door is swung arcuately upwardly, so that the space necessary for the pivoting motion of the door is reduced to a minimum.

Further features of the present invention are that a guide pin is provided on each of the levers and a bracket is provided on the bunker for each of the levers. The bracket is partly provided, on its outside, with a guide surface having a slot in which the lever is guided during the swinging motion. The guide pin can apply from the outside against the guide surface. Due to this guide surface and the guide pin, the door is prevented during the closing motion from applying in some way against the edge of the discharge opening. In front of the discharge opening, the door is exactly guided into its closing position.

Accordingly, it is an object of the invention to provide a bunker closure door mechanism for a bunker having a housing with an opening and a seat defined around the opening which is closed by a door body and, wherein, the door body is supported by first and second spaced apart end levers which are pivotally connected to the housing and engage the door adjacent one end thereof and also by first and second central levers which are pivotally connected to the door body intermediate its length and have opposite ends which are pivotally connected to the ends of toggle levers of a shorter length than the central levers which are pivotally mounted on the bunker housing, the central levers being shiftable by an actuator which engages the central lever to shift the toggle lever beyond the dead center position when opening the door body and, wherein, the door body has a guide pin which is guided on a guide member of the housing so that, initially, the movement of the toggle lever loosens the door and permits the downward shifting movement thereof and, thereafter, the pivotal movement about the end levers into a position to one side of the bunker opening.

A further object of the invention is to provide a bunker closure door operating mechanism which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
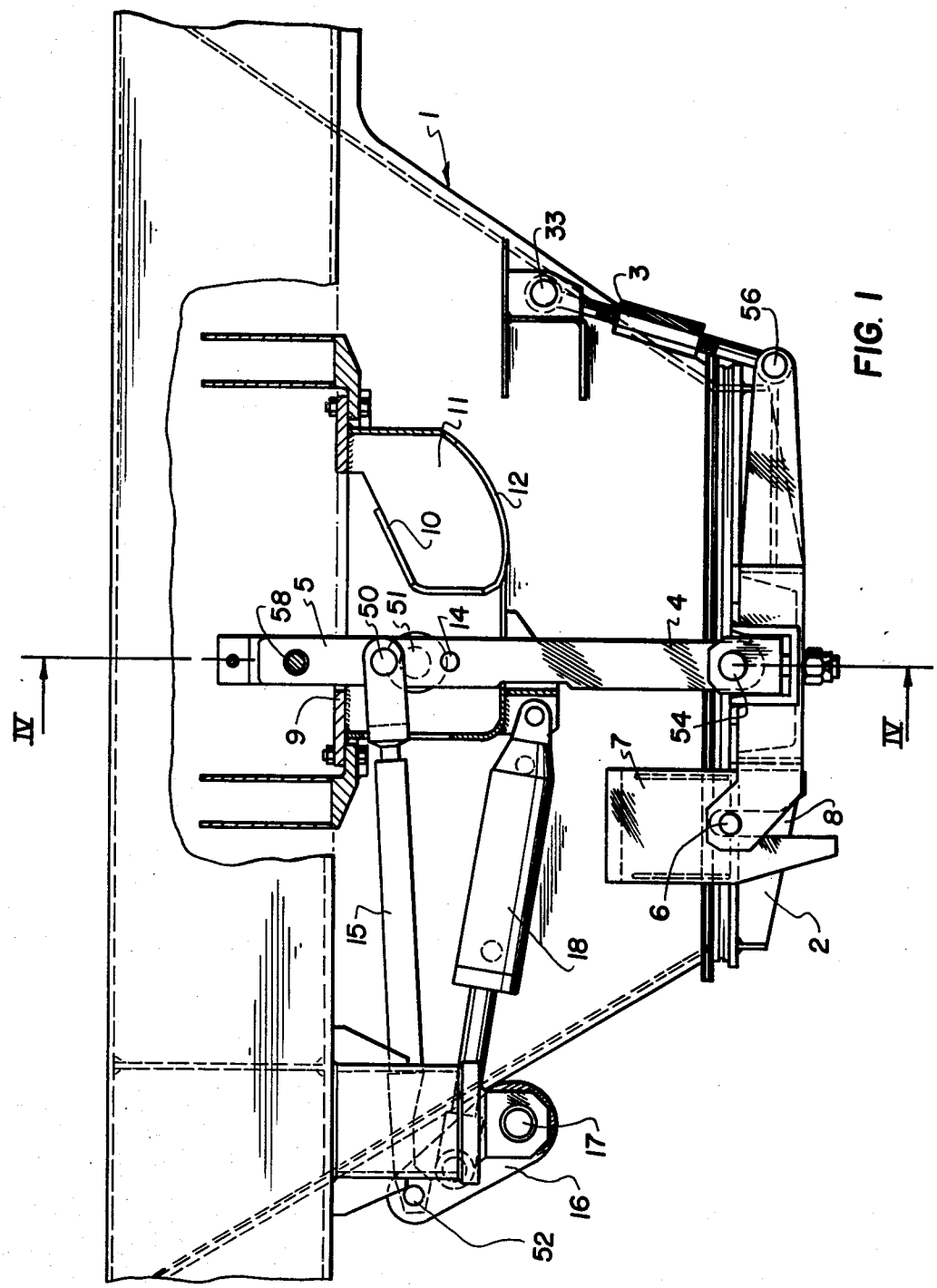
FIG. 1 is a partial side elevational view and partial sectional view of a bunker having a closure door operating mechanism constructed in accordance with the invention.

Referring to the drawings in particular, the invention embodied therein, comprises, a bunker door closure mechanism for a so-called shipping bunker, which includes a bunker housing 1, having an opening 40 for the discharge of material with a seat 42 around the opening which is closed by a bunker door body, generally designated 12.

The lower part of the shipping bunker 1 is of a funnel-shaped configuration and the vertically downwardly directed opening is closable by means of the door body 2. One end of the door body 2 is hinged to end links 3, 3, which are parallel to and spaced from each other and hinged, by their other ends by pivots 33 to bunker 1. At approximately the middle of its length, and on its outside, door 2 is provided with central levers 4, 4 which extend in parallel to each other and are each hinged at one end to a pivot 44 carried by the door 2 and at each other end to a corresponding free end of respective toggle levers 5, 5 which, in turn, are pivoted at 51 to bunker 1. More outwardly, near its end remote from links 3, door 2 is provided with guide pins 6, 6 which project to the outside. These guide pins 6 are each guided in a vertical guide slot 8 of a guide member 7 which is fixed to bunker 1. The slots 8 of guide members 7 are open downwardly.

The pivotal path of each of the toggle levers 5 is limited by stops 9 and 10 and the design is such that while applying against stop 9, lever 5 is in a position beyond its top dead center. For each of the central levers 4, bunker 1 is further provided with a bracket 11 which, on its outside, is partly provided with a guide surface 12 which, in turn, is provided with a slot 13 for guiding lever 4. Each of the levers 4 is provided with a guide pin 14 which, during the pivotal motion of lever 4, can apply from the outside against guide surface 12 of bracket 11.

Further, a guide rod 15 is hinged by a pin 50 to, and acts upon, lever 4 and is hinged, by a pin 52 at its free end, to a respective lever 16, 16. Levers 16, 16 are rotatably secured at spaced locations to a shaft 17 which extends horizontally and transversely of bunker 1 and is mounted thereon for pivoting. Levers 16 at both sides of bunker 1 are non-rotatably connected to each other by shaft 17. Actuating means includes a working cylinder 18 which is hinged to and acts upon one of the levers 16 and is hinged, by its other end, to bracket 11. Working cylinder 18 can be operated either hydraulically or pneumatically.

Figure 2:
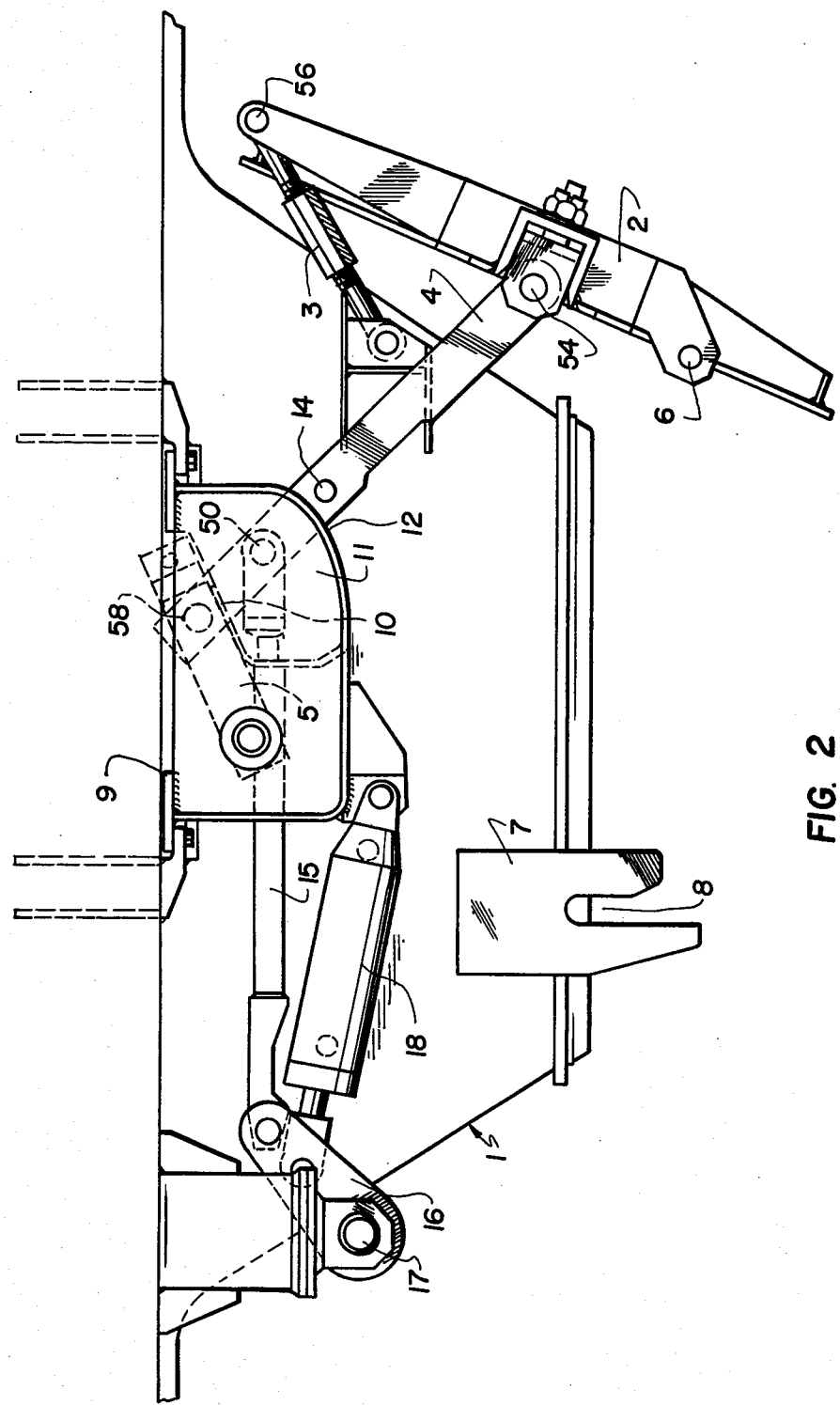
FIG. 2 is a view, similar to FIG. 1, showing the opened position of the bunker door.
Figure 3:
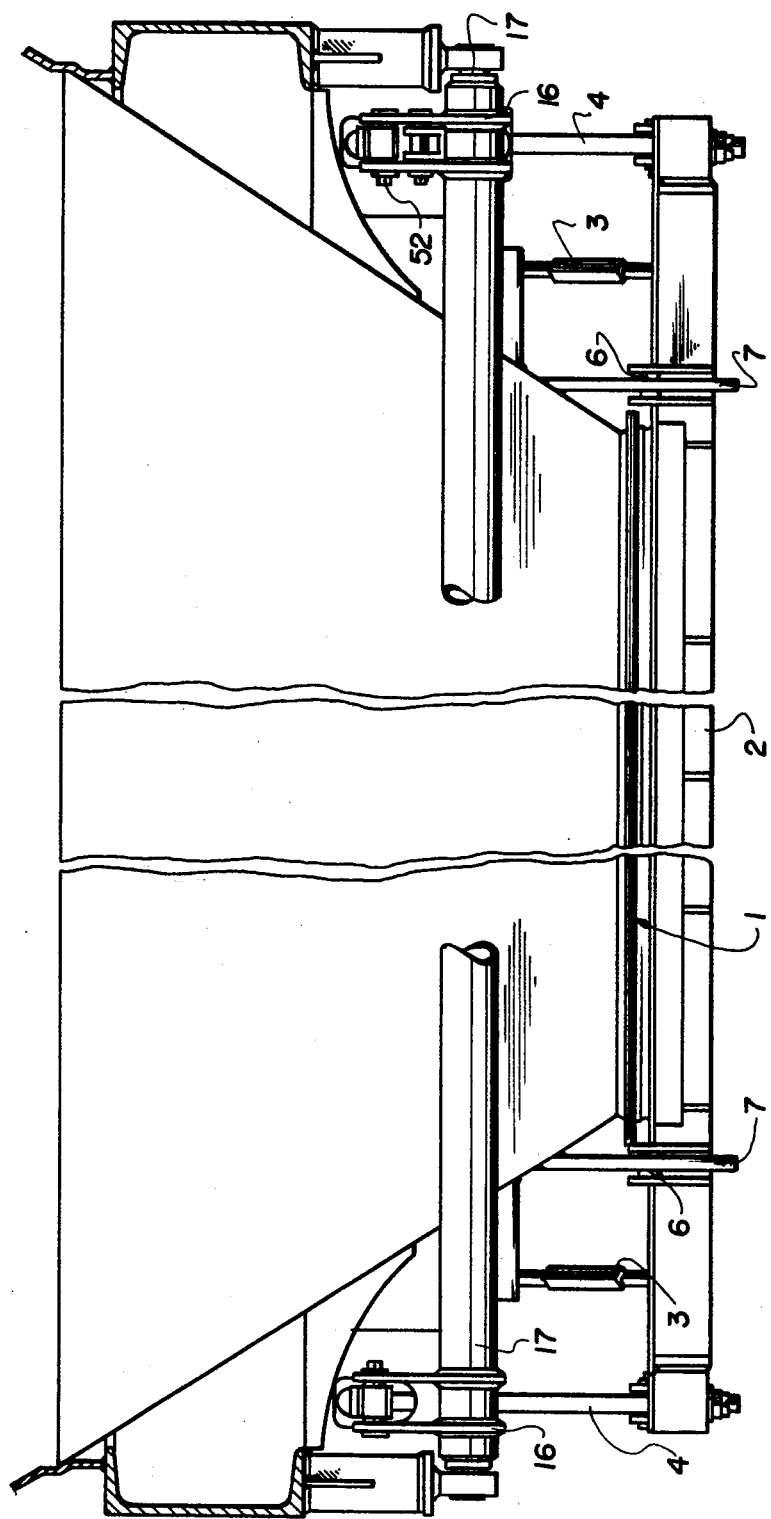
FIG. 3 is a front view of the bunker shown in FIG. 1.
Figure 4:
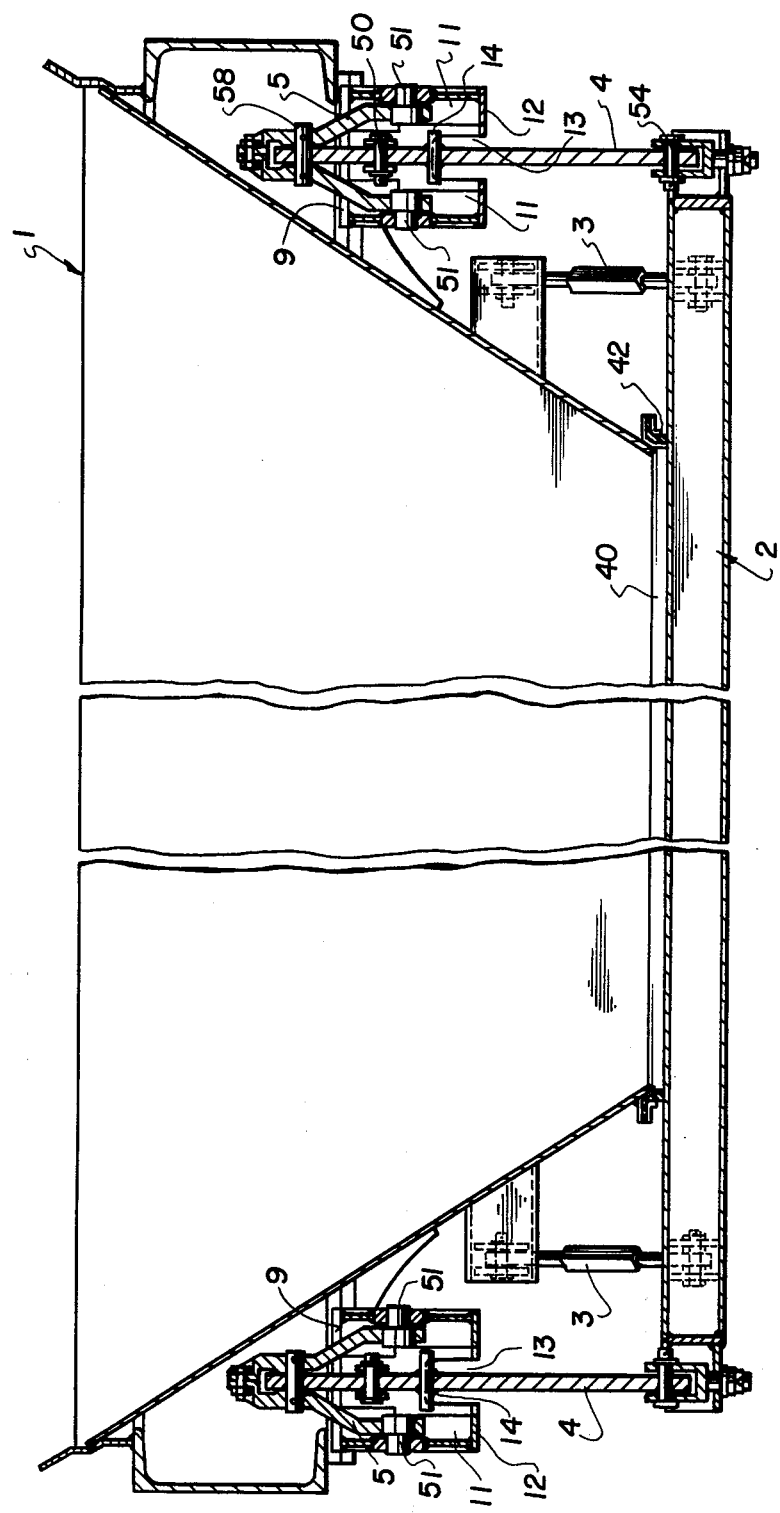
FIG. 4 is a section taken along the line IV—IV of FIG. 1.

To open the door body 2, lever 16 is pivoted by means of the working cylinder 18. Through guide rod 15, lever 16 acts on lever 4 which, in the first phase of the opening motion, is held in position through its lower end and door 2 by guide pins 6, 6 which are engaged in guide slots 8 of guide members 7. In its further motion, lever 4 first causes a pivotal motion of lever 5 to the righthand side, as viewed in FIGS. 1 and 2, beyond the top dead center thereof. The downward pivoting of lever 5 then causes a vertical downward movement of lever 4 and of its hinge point 54 with door 2. The free end of door 2 which is hinged at 56 by its other end to links 3, is thereby moved vertically downwardly while being guided by guide pins 6, until guide pins 6 disengage from guide slots 8 of the guide members 7. In this position of the door, lever 5 rests against the stop 10. During the further pivoting of lever 16 by the action of guide rod 15, lever 4 is swung sideways about its hinge point 58 with lever 5, which now acts as a fixed point. In this motion, door 2 is guided by lever 4 and links 3 and is swung sideways into a position laterally of the discharge opening of the bunker.

The closing of door 2 is effected in the reverse order. If unobstructed, door 2 in the open position, shown in FIG. 2, hangs down by its own weight, so that lever 5 rests against stop 10. In the event the hinge points of lever 4 or links 3 with door 2 become jammed by the material or some other manner, which would result in a lifting of lever 5 during the pivotal motion of the door into its closing position, guide pin 14 applies against guide surface 12 of bracket 11, whereby, lever 4, guided in slot 13 of bracket 11, is guided by guide pin 14 arcuately in the closing direction. The guide pin 14 disengages from guide surface 12 as soon as guide pins 6 come into a position below guide slot 8 of guide members 7. During a further pivoting of lever 16, lever 5 and, thereby, lever 4 and door 2 are lifted until door 2 engages the discharging opening. Lever 5 which has now been brought into a position beyond its top dead center, secures door 2 mechanically against opening.

While a specific embodiment of the invention has been shown and described in detail to illustrate the application of the principles of the invention, it will be understood that the invention may be embodied otherwise without departing from such principles.

What is claimed is:

1. A bunker closure door mechanism, for a bunker having a housing with an opening for the discharge of material, and with a seat around the opening, comprising, a closure door body adapted to be engaged on the seat to close the opening, first and second spaced apart end levers each having one end pivotally connected to the bunker housing and having an opposite end pivotally connected to said door body at respective sides and adjacent one end of said door body, guide means on said housing defining a stabilizing guideway to control operation of the closure door, first and second central levers each having one end pivotally connected to said door body adjacent respective sides thereof and intermediate the length of said door body and having respective opposite ends, first and second toggle levers each having one end pivotally connected to the housing and an opposite end pivotally connected to the respective ends of said central levers, actuator means pivotally connected to said central levers intermediate their lengths to pivot said central levers about their connections to said toggle levers, guide pin means on said door body between the pivotal connection of said central levers to said door body and the end of said door body which is opposite to the connections of said end levers to said door body, said guide pin means being engageable in said guideway, during opening of said door body by said actuator means, whereby, in the initial stage, said pins hold said door body against lateral movement and permit the lowering thereof, said toggle levers being pivoted by said actuator means beyond the top dead center position thereof to permit downward movement of said door body, further movement of said actuator means being effective to move said central levers with said door body to one side of the housing.

2. A bunker closure door mechanism, as claimed in claim 1, wherein said guide means includes a member defining a vertically enlongated slot opening downwardly toward said door body, said guide pin means comprising a pin carried by said door body engageable in the slot and being movable vertically in the slot when it is confined therein, but being disengageable downwardly from said slot after a predetermined amount of vertical movement.

3. A bunker closure door mechanism, as claimed in claim 1, including first and second stops carried by said housing on each side of said toggle levers limiting the amount of movement of said toggle levers between said stops, said stops being located in a position to permit movement of the lever beyond the top dead center position between said stops, said guide means confining said pin guide means for substantially vertical movement of said pin guide means and said door body and being disengageable when said toggle lever is moved into engagement with one of said stops.

4. A bunker closure door mechanism, as claimed in claim 1, wherein said guide means on said housing comprises a plate member having a vertically elongated downwardly opening slot, said guide pin means on said door body comprising a pin extending laterally outwardly from each side of said door engageable into a respective slot and holding said door body against displacement until said pin is lowered out of the bottom of said slot during opening of the door body.

5. A bunker closure door mechanism, as claimed in claim 1, wherein said actuator means comprises a rotatable shaft, a crank lever affixed to said shaft for rotation thereby, a fluid pressure operated piston and cylinder combination having one end hingedly connected to said housing and an opposite end connected to said crank lever for shifting said lever and rotating said shaft, and a guide rod connected between said crank lever and said central levers.

* * * * *